US012616384B2

(12) United States Patent
Liu et al.

(10) Patent No.: US 12,616,384 B2
(45) Date of Patent: *May 5, 2026

(54) CARDIAC DIASTOLIC FUNCTION ASSESSMENT METHOD, DEVICE AND SYSTEM

(71) Applicant: SHENZHEN DARMA TECHNOLOGY CO., LTD., Shenzhen (CN)

(72) Inventors: Pengbo Liu, Shenzhen (CN); Shaochun Zhuang, Shenzhen (CN); Lingjun Zeng, Shenzhen (CN); Zhengpei Chu, Shenzhen (CN)

(73) Assignee: CARDIOSTORY INC., Lewes, DE (US)

( * ) Notice: Subject to any disclaimer, the term of this patent is extended or adjusted under 35 U.S.C. 154(b) by 1041 days.

This patent is subject to a terminal disclaimer.

(21) Appl. No.: 17/613,037

(22) PCT Filed: May 20, 2019

(86) PCT No.: PCT/CN2019/087642

§ 371 (c)(1),
(2) Date: Nov. 19, 2021

(87) PCT Pub. No.: WO2020/232607

PCT Pub. Date: Nov. 26, 2020

(65) Prior Publication Data

US 2022/0248963 A1 Aug. 11, 2022

(51) Int. Cl.
| | |
|---|---|
| *A61B 5/021* | (2006.01) |
| *A61B 5/11* | (2006.01) |
| *A61B 5/318* | (2021.01) |

(52) U.S. Cl.
CPC ................ *A61B 5/021* (2013.01); *A61B 5/11* (2013.01); *A61B 5/318* (2021.01);
(Continued)

(58) Field of Classification Search
CPC ........... A61B 5/021; A61B 5/11; A61B 5/318; A61B 2562/0219; A61B 2562/0247;
(Continued)

(56) References Cited

U.S. PATENT DOCUMENTS

| | | | | | |
|---|---|---|---|---|---|
| 2001/0039385 | A1* | 11/2001 | Ellenz | .................... | A61B 5/335 |
| | | | | | 600/524 |
| 2005/0027204 | A1* | 2/2005 | Kligfield | ................ | A61B 5/318 |
| | | | | | 600/510 |

(Continued)

FOREIGN PATENT DOCUMENTS

| | | | | | | |
|---|---|---|---|---|---|---|
| CA | 2341450 | A1 | * | 3/2000 | ........... | A61B 5/7239 |
| CA | 2668602 | A1 | * | 5/2007 | ........... | A61B 5/4809 |

(Continued)

*Primary Examiner* — Jason M Sims
*Assistant Examiner* — Matthew Eric Ogles
(74) *Attorney, Agent, or Firm* — Cheng-Ju Chiang

(57) ABSTRACT

Disclosed is a cardiac diastolic function assessment method applicable to the field of cardiac monitoring. The method comprises: acquiring vibration information of the thoracic cavity body surface of an object in a noninvasive manner; preprocessing the vibration information to generate hemodynamic-related information; determining a target wave group on the basis of the hemodynamic-related information; determining the highest peak on the target wave group, determining a rising edge amplitude before the highest peak as a first characteristic value, and determining, as a second characteristic value, an amplitude between the highest peak and the subsequent lowest valley; and generating an indicating parameter on the basis of the first characteristic value and the second characteristic value, and assessing a cardiac diastolic function of the object on the basis of the indicating parameter.

13 Claims, 8 Drawing Sheets time

(52) U.S. Cl.
CPC ................. *A61B 2562/0219* (2013.01); *A61B 2562/0247* (2013.01); *A61B 2562/0261* (2013.01)

(58) Field of Classification Search
CPC .......... A61B 2562/0261; A61B 5/6892; A61B 5/6823; A61B 5/02108; A61B 5/02028; A61B 5/1102; A61B 5/02116; A61B 5/02133; A61B 5/024; A61B 5/0261; A61B 5/029; A61B 5/0205; A61B 5/346; A61B 5/349; A61B 2562/0233; A61B 2562/0266; A61B 2562/04; A61B 5/6887; A61B 5/6891
See application file for complete search history.

(56) References Cited

U.S. PATENT DOCUMENTS

| | | | | |
|---|---|---|---|---|
| 2005/0240112 A1* | 10/2005 | Fang | ...................... | A61B 5/349 |
| | | | | 600/509 |
| 2009/0227886 A1* | 9/2009 | Bauer | .................... | A61B 7/006 |
| | | | | 600/528 |
| 2010/0249629 A1 | 9/2010 | Schmidt et al. | | |

| | | | | |
|---|---|---|---|---|
| 2011/0230788 A1* | 9/2011 | Anand | ................. | A61B 5/4528 |
| | | | | 600/587 |
| 2012/0203117 A1* | 8/2012 | Chen | .................... | A61B 5/7214 |
| | | | | 600/595 |
| 2013/0046190 A1* | 2/2013 | Davies | ............... | A61B 5/02007 |
| | | | | 600/486 |
| 2013/0137997 A1* | 5/2013 | Patangay | ............... | A61B 5/746 |
| | | | | 600/513 |
| 2015/0182141 A1* | 7/2015 | Fujita | ................... | A61B 5/7275 |
| | | | | 600/500 |
| 2015/0313533 A1* | 11/2015 | Rapp | .................... | A61B 5/0082 |
| | | | | 600/476 |
| 2017/0105642 A1* | 4/2017 | Chen | ...................... | A61B 5/316 |
| 2018/0289288 A1* | 10/2018 | Kim | ................... | A61B 5/02108 |
| 2018/0360315 A1* | 12/2018 | Fujita | .................. | A61B 5/7246 |
| 2022/0218208 A1* | 7/2022 | Zeng | ................... | A61B 5/0261 |
| 2022/0248962 A1* | 8/2022 | Chu | .................... | A61B 5/7267 |

FOREIGN PATENT DOCUMENTS

| | | |
|---|---|---|
| CN | 107595278 A | 1/2018 |
| CN | 107822608 A | 3/2018 |
| CN | 108354612 A | 8/2018 |
| CN | 109222928 A | 1/2019 |
| CN | 109310371 A | 2/2019 |

* cited by examiner

100

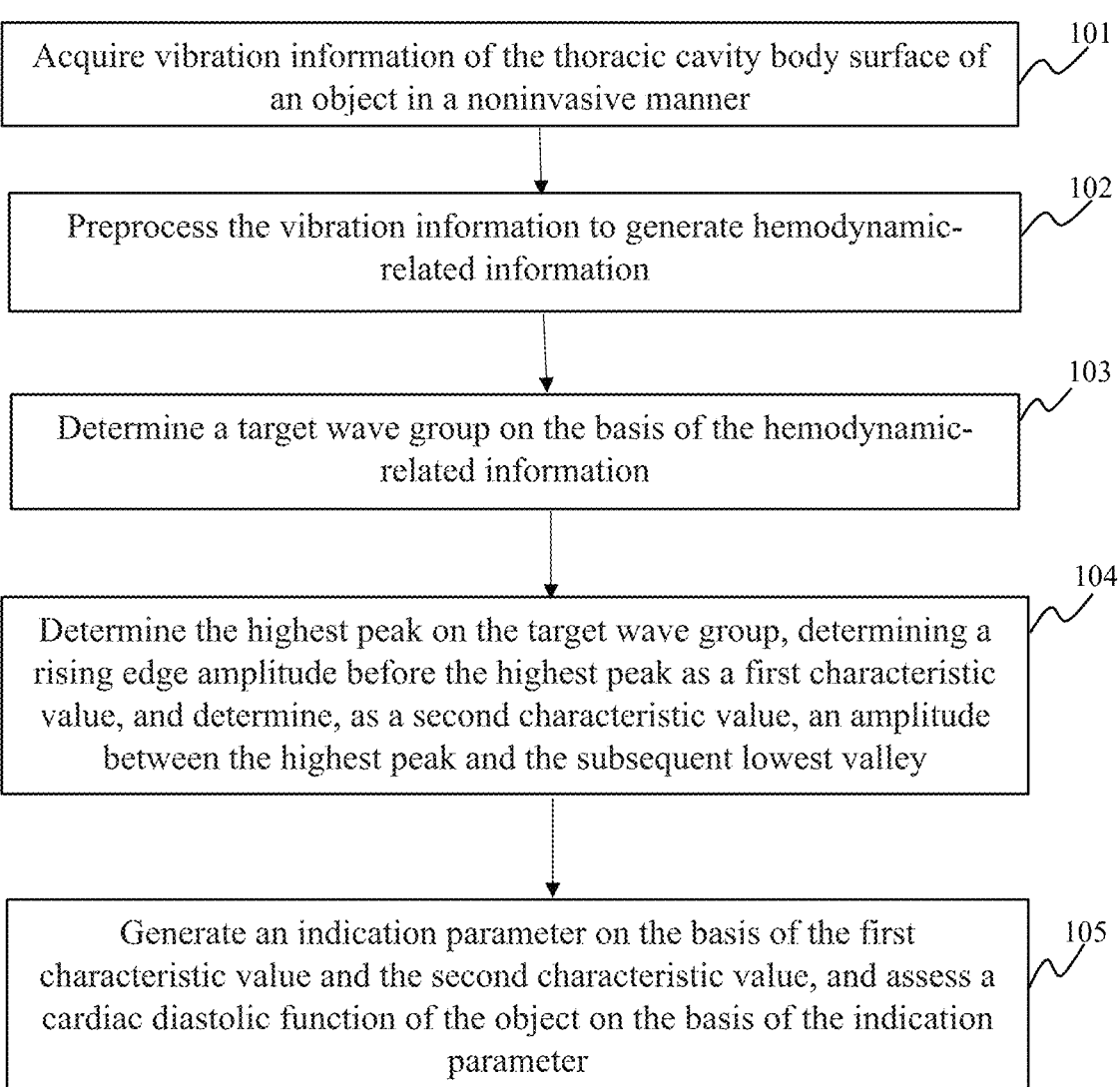

Acquire vibration information of the thoracic cavity body surface of an object in a noninvasive manner ⟶ 101

Preprocess the vibration information to generate hemodynamic-related information ⟶ 102

Determine a target wave group on the basis of the hemodynamic-related information ⟶ 103

Determine the highest peak on the target wave group, determining a rising edge amplitude before the highest peak as a first characteristic value, and determine, as a second characteristic value, an amplitude between the highest peak and the subsequent lowest valley ⟶ 104

Generate an indication parameter on the basis of the first characteristic value and the second characteristic value, and assess a cardiac diastolic function of the object on the basis of the indication parameter ⟶ 105

FIG. 1 time time time time time time time time

1

CARDIAC DIASTOLIC FUNCTION ASSESSMENT METHOD, DEVICE AND SYSTEM

CROSS REFERENCE TO RELATED APPLICATIONS

The present application is a 35 U.S.C. § 371 National Phase conversion of International (PCT) Patent Application No. PCT/CN2019/087642, filed on May 20, 2019, the disclosure of which is incorporated by reference herein. The PCT International Patent Application was filed and published in Chinese.

FIELD OF THE INVENTION

The present invention relates to the field of cardiac monitoring, and particularly relates to a non-invasive diastolic function assessment method, device and system.

BACKGROUND OF THE INVENTION

Heart failure (abbreviated as HF) is a clinical syndrome with multiple etiologies and pathogenesis. With the aging of the population and an increasing survival rate of patients with acute myocardial infarction, the number of patients with chronic heart failure is increasing rapidly. Patients with heart failure suffer from a chronic state to an acute worsening state, and suffer from an accompanied deterioration of diastolic function, such as an elevated filling pressure. Elevated filling pressure will cause the heart's function to enter a rapid vicious circle, but the patient itself will not feel the symptoms until the filling pressure continues to rise for about 20 days and need to be admitted to the hospital urgently; while at this time, the impairment of the heart function is caused and is irreversible. When the patient is identified in an elevated filling pressure status, timely intervention is required to avoid further deterioration. This has become the consensus of clinicians.

At present, there are implantable products used to evaluate the diastolic function, but the cost is relatively high, and if it is only used for monitoring, patients are less likely to accept. Therefore, a more friendly and more convenient product is needed for monitoring the diastolic function.

SUMMARY OF THE INVENTION

Technical Problem

An object of the present invention is to provide a method, device, system, and computer-readable storage medium for accessing a cardiac diastolic function of a subject.

Solutions to the Problem

Technical Solutions

In a first aspect, the present invention provides a cardiac diastolic function assessment method, comprising steps of:
  acquiring vibration information on a body surface corresponding to a subject's thoracic cavity in a noninvasive manner;
  preprocessing the vibration information to generate hemodynamic related information;
  determining a target wave group based on the hemodynamic related information;

determining the highest peak on the target wave group;
    determining a rising edge amplitude before the highest peak as a first characteristic value; and determining an amplitude between the highest peak and the subsequent lowest valley as a second characteristic value; and
  generating an indicating parameter based on the first characteristic value and the second characteristic value; and assessing a diastolic function of the subject based on the indicating parameter;
  In a second aspect, the present invention provides a computer-readable storage medium having computer programs stored thereon, which when being executed by a processor, cause the processor to perform the steps of the above-mentioned cardiac diastolic function assessment method.

In a third aspect, the present invention provides a diastolic function assessment device, comprising: one or more processors; a memory; and one or more computer programs, wherein the one or more computer programs are stored in the memory, and configured to be executed by the one or more processors; and the one or more processors execute the one or more computer programs to perform the steps of the above-mentioned diastolic function assessment method.

In a fourth aspect, the present invention provides a cardiac diastolic function assessment system, comprising:
  one or more vibration sensors for acquiring vibration information on a body surface corresponding to a subject's thoracic cavity surface; and
  the diastolic function assessment device, as described above, connected to the one or more vibration sensors.

Advantages of the Preset Invention

Advantages

The method of the present invention monitors the diastolic function by acquiring the vibration information of the subject without intruding his body, it is a passively measuring, and can realize continuous monitoring. The subject only needs to lie on the measuring device to perform the measurement, and no need for professional assistance. The method has the advantages of high measurement accuracy and simple operation, can improve the comfort of the tester, and can be applied to scenes such as hospitals and homes. The diastolic function assessment system provided in the present invention can evaluate the diastolic function of the subject, and then prompt a warning in advance when deterioration appear, so as to help the subject avoid deterioration.

BRIEF DESCRIPTION OF THE DRAWINGS

FIG. 1 is a flowchart of a diastolic function assessment method in accordance with a first embodiment of the present invention;

DETAILED DESCRIPTION OF THE INVENTION

Figure 2:
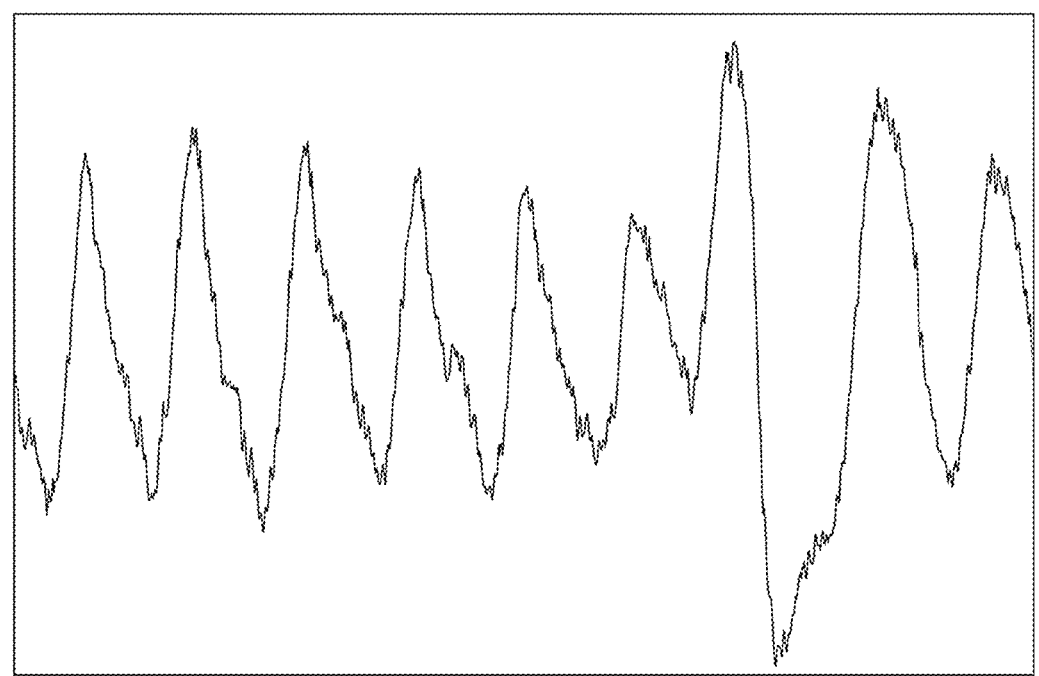
FIG. 2 is a waveform diagram of vibration information of the subject A acquired by a fiber-optic sensor.

In order to make the objects, technical solutions, and advantages of the present invention clearer, the present invention will be further described in detail below in conjunction with the accompanying drawings and embodiments. It should be understood that the specific embodiments described here are only used to explain the present invention, but not to limit the present invention.

As used in the description and claims, the terms "a", "an" and "the" comprise both singular and plural references unless the context clearly dictates otherwise. Generally, the term "includes" or "comprise" is intended to mean the steps or elements that have been clearly identified, and these steps or elements do not constitute an exclusive list, and the method or device can also comprise other steps or elements.

In order to illustrate the technical solutions of the present invention, the following is explained through specific embodiments.

First Embodiment

Referring to FIG. 1, a diastolic function assessment method 100 provided in the first embodiment of the present invention comprises the following steps. It should be noted that if there are substantially the same results, the diastolic function assessment method of the present invention is not limited to the flowchart sequence shown in FIG. 1.

S101, acquiring vibration information on a body surface corresponding to a subject's thoracic cavity in a noninvasive manner.

In the first embodiment of the present invention, in the step of acquiring vibration information on a body surface corresponding to a subject's thoracic cavity in a noninvasive manner, one or more vibration sensors may be used. Vibration information can be acquired through acceleration sensors, pressure sensors, displacement sensors, etc., or sensors that convert physical quantities equivalently based on acceleration, pressure, and displacement (such as electrostatic sensors, inflatable pressure sensors, fiber-optic sensors etc.). When acquiring signals, the vibration sensor is generally configured to be placed under the body of the supine subject. For example, the vibration sensor can be placed on the bed, and the subject can rest thereon in a supine, prone, or side-lying posture. Taking the subject in a supine position as an example, a preferable measurement position is that the fiber-optic sensor is configured to be placed under the subject's back, for example, under the back body surface corresponding to the first thoracic vertebra to the twelfth thoracic vertebra, specifically below the right shoulder blade. Generally, in order to ensure the quality of the signals, the vibration sensor is configured to be placed under the right shoulder of the subject, specifically around the right shoulder blade, and the subject needs to be measured in a supine position in a quiet state. Those of ordinary skill in the art can understand that when the subject lies in a prone position, the measurement position is the subject's chest which corresponds to the back in the supine position. In addition, the vibration sensor can also be placed on a contact surface behind the back of the subject lying in a supine at a certain tilt angle or a contact surface behind the back of the subject leaning on a wheelchair or leaning on other leaning objects to acquire the vibration information.

At least one vibration sensor is used in the present invention. When multiple vibration sensors are used, each sensor works independently and synchronously. The size of each sensor can be the same or different, such as 20 cm*30 cm or 5 cm*4 cm. Sensors with any size can be arranged and combined in any way. For example, in some embodiments, a thinner subject can be provided with one large sensor or two small sensors, while a subject with a wider body can be provided with two large sensors or a combination of two small sensors and one large sensor. When a fiber-optic sensor is used as the vibration sensor, at least one fiber-optic sensor is placed under the right shoulder of the subject. The fiber-optic sensor can be placed directly under the subject's body or placed under a mattress in indirect contact with the subject. In some examples, a sense area of the fiber-optic sensor is at least 20 square centimeters, where the sense area refers to the area of the vibration sensor actually used to sense vibration (for example, the sense area of a fiber-optic sensor refers to the area where the optical fibers are distributed in the fiber-optic sensor).

FIG. 2 shows the original signal waveform of the subject A acquired by a fiber-optic sensor, where the horizontal axis represents time, and the vertical axis represents normalized vibration information, which is dimensionless. Since the sensor acquires vibration signals, the acquired raw data contains not only the subject's breathing signal and hemodynamic signal, but also the interferences caused by environmental micro-vibration and body movement, as well as the noise signal of the circuit itself. The vibration sensor used in this embodiment is a fiber-optic sensor, which is sensitive to changes in vibration displacement. An outline of signals is the signal envelope generated by the subject's breathing, and the hemodynamic signal, interferences and noises are superposed on the curve of breathing envelope.

S102, preprocessing the vibration information to generate hemodynamic related information.

The vibration signals acquired by different sensors contain different information, and some sensors acquire relatively rich information, so the acquired information need to be preprocessed to obtain desired signals. For example, when a fiber-optic sensor is used as the vibration sensor, the acquired vibration signals comprise the subject's breathing signal, body motion signal, hemodynamic signal, inherent noise of the sensor circuit, and environmental micro-vibration signals.

In the first embodiment of the present invention, S102 may specifically comprise:

performing at least one of filtering, noise removal and signal scaling on the vibration information to obtain hemodynamic related information. Specifically, according to the desired characteristics of the filtered signal, one or more combinations of: low-pass filtering, band-pass filtering, IIR (Infinite Impulse Response) filtering, FIR (Finite Impulse Response) filtering, wavelet filtering, zero-phase bidirectional filtering, polynomial smoothing filtering, integral transformation, and differential transformation, can be used to filter vibration information at least once; for example, filtering the vibration information below 1 Hz to remove breathing signals and body motion signals. Preprocessing may also comprise steps of: determining whether the vibration signal carrying power-line interference, and if yes, using a power frequency filter to remove power-line interference; or, further, removing high-frequency interference (for example, above 45 Hz). The processed information can be scaled according to specific conditions to obtain the hemodynamic related information. Or, filtering the vibration signal by directly setting a filter interval such as any interval between 1 Hz-50 Hz.

Figure 3:
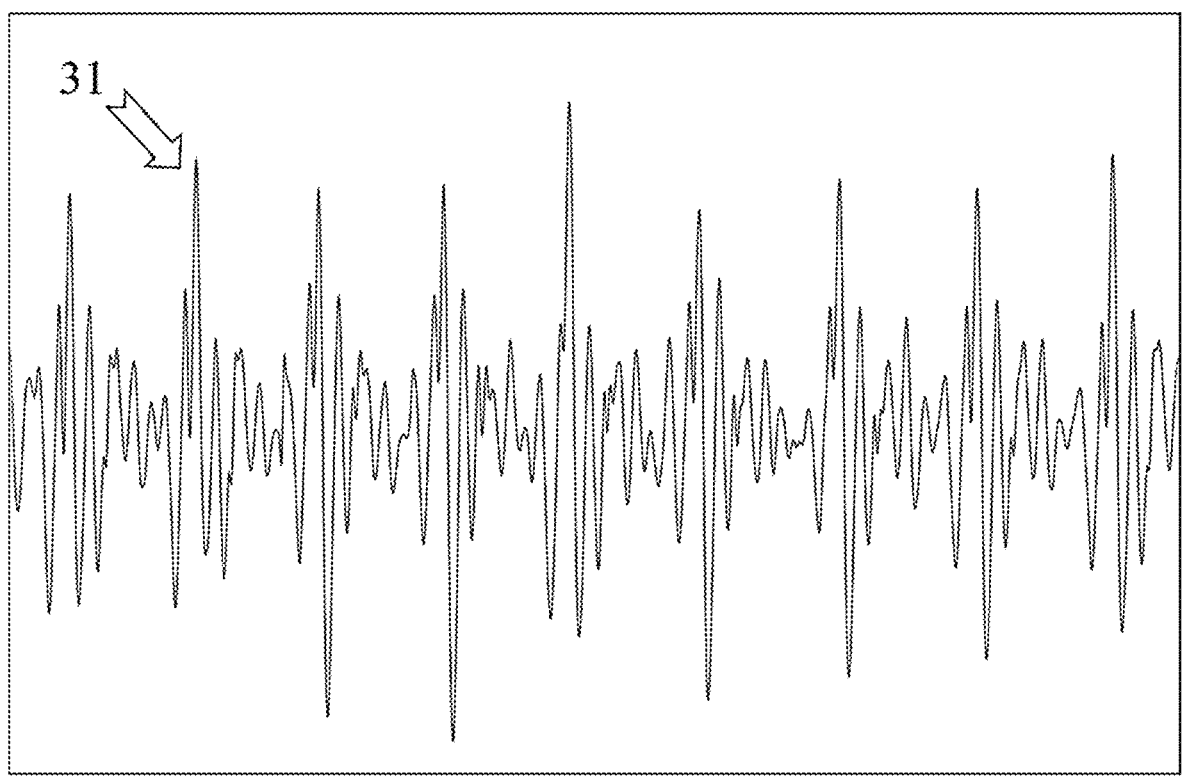
FIG. 3 is a diagram of time-domain waveforms of hemodynamic related information.

FIG. 3 illustrates a time-domain waveform diagram of high-quality hemodynamic related information after preprocessing the vibration information acquired by the fiber-optic sensor, and a filtering interval of the curve 31 is 2 Hz-45 Hz. Each waveform of curve 31 has obvious characteristics and good consistency, periodicity, stable baseline, and clear outline. Here, what we need is an orderly, regular, and cyclical heartbeat. The above-mentioned heartbeats with obvious characteristics in a stable state, can more accurately reflect and reveal the ventricular diastolic function of the subject's current state, and the reliability is higher.

S103, determining a target wave group based on the hemodynamic related information.

In the first embodiment, S103 may specifically comprise steps of S1031 to S1033.

S1031, performing high-frequency component extraction on the hemodynamic related information to generate high-frequency component information.

A cycle beating of the heart will cause periodic phenomena of various changes, such as periodic changes in intra-cardiac pressure and cardiovascular pressure, the volume of both atria and the ventricles, opening and closing of the heart valves (including mitral valve, tricuspid valve, aortic valve, pulmonary artery), and blood flow velocity, etc. These periodic changes drive blood flowing in a certain direction in the circulatory system. Hemodynamics (hemodynas) studies mechanics of blood flow in the cardiovascular system, and it takes blood flow and the blood vessel deformation as the research objects. The "hemodynamic related information" described in the present invention refers to any information related to hemodynamics, and may comprise, but is not limited to, one or more of: information related to producing blood flow (for example, atrial contraction and relaxation causes ejection), information related to the dynamics of blood flow (such as CO (cardiac output), left ventricular ejection impacting the aortic arch), information related to blood flow pressure (such as systolic blood pressure, diastolic blood pressure, mean arterial pressure, venous filling pressure, etc.), and blood vessel-related information mation (such as blood vessel elasticity, etc.). The periodic beating of the heart can maintain blood circulation. Therefore, various parameters related to heartbeats, such as the opening and closing of the heart valve, the changes in the volume of both the atria and ventricles, the changes in the pressures of the atria and the ventricles, and the flow rate and direction of blood flow in the atria and ventricles. et., which are all hemodynamic related information.

Vibration information essentially corresponds to acceleration, velocity, and displacement changes, and the vibration information obtained through the fiber-optic sensor essentially corresponds to displacement changes, which are relatively smooth. Some details changes in acceleration or velocity are difficult to identify in the displacement change information. For example, the velocity gradually increases from zero to a certain peak value, and then gradually decreases from the peak value to zero. The velocity change curve forms a waveform that first rises and then drops, while the displacement change curve presents only an ascending waveform. Therefore, compared to the signal component corresponding to the displacement, the peak-to-valley time width of the signal component corresponding to the velocity and acceleration is narrower, which may be called high-frequency component information. The high-frequency component extraction method may comprises performing polynomial fitting and smoothing filtering, or performing differentiation on hemodynamic related information to generate high-frequency component information. For example, S1031 may specifically be: performing first-order differential processing on hemodynamic related information to generate first high-frequency component information, and performing second-order differential processing to generate second high-frequency component information.

In addition, the vibration information acquired by the acceleration sensor essentially corresponds to hemodynamic acceleration change information, that is, the second high-frequency component information. At this time, the acceleration change information can be processed by first-order integration to generate the first high-frequency component information.

Other types of sensors, such as radar waves, essentially sense the changes in vibration displacement of the subject's body, those of ordinary skill in the art can understand that, the signal processing method thereof can use the above-mentioned signal processing process of the fiber-optic sensor, which is also within the protection scope of the present invention.

Figure 4:
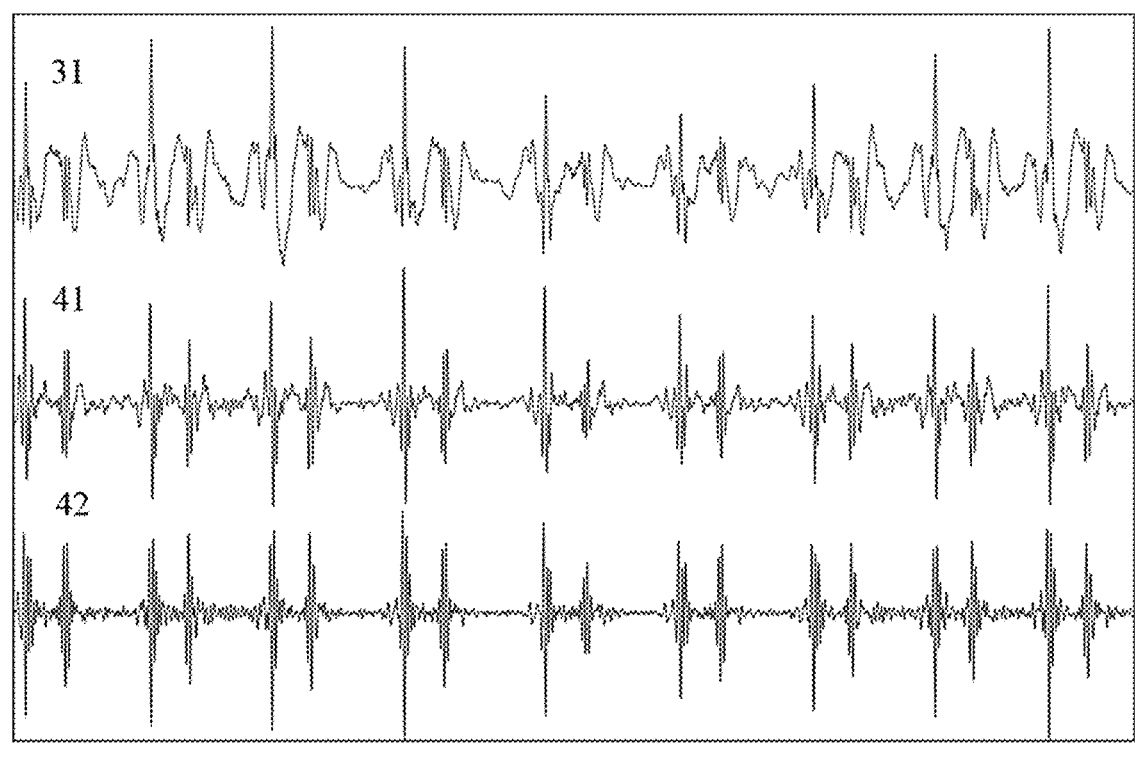
FIG. 4 is a diagram of time-domain waveforms of the hemodynamic related information, first high-frequency component information, and second high-frequency component information which are located on the same time axis.

As shown in FIG. 4, the curve 41 is the time-domain waveform curve of the first high-frequency component information, and the curve 42 is the time-domain waveform curve of the second high-frequency component information. The selected frequency band of the band-pass filter for each curve is 2 Hz-45 Hz, the horizontal axis represents time, and the vertical axis is dimensionless. Curve 41 and curve 42 are waveform curves after performing first-order differential processing and second-order differential processing on curve 31, where curve 31 of the hemodynamic related information, curve 41 of the first high-frequency component, and curve 42 of the second high-frequency component are synchronously displayed on the same time axis.

S1032, synchronizing the hemodynamic related information, the first high-frequency component information, and the second high-frequency component information on the same time axis, and performing heartbeat segmentation.

In some examples, when the vibration information is continuously acquired, the hemodynamic related information, the first high-frequency component information, and the second high-frequency component information generated by processing the vibration information are also continuous data, thereby heartbeat segmentation is needed. The heartbeat segmentation can be performed based on the repetitive characteristics in the waveforms of: hemodynamic related information, the first high-frequency component information, or the second high-frequency component information. Since the heart activity has obvious periodicity, there are some obvious characteristics that have high repetitiveness. For example, the cardiac cycle of a normal person is between 0.6 s and 1 s, a search interval can be set accordingly, then search for the highest peak, and use the highest peak as a heartbeat segmentation feature. Similarly, the lowest valley can also be used as a heartbeat segmentation feature.

Figure 5:
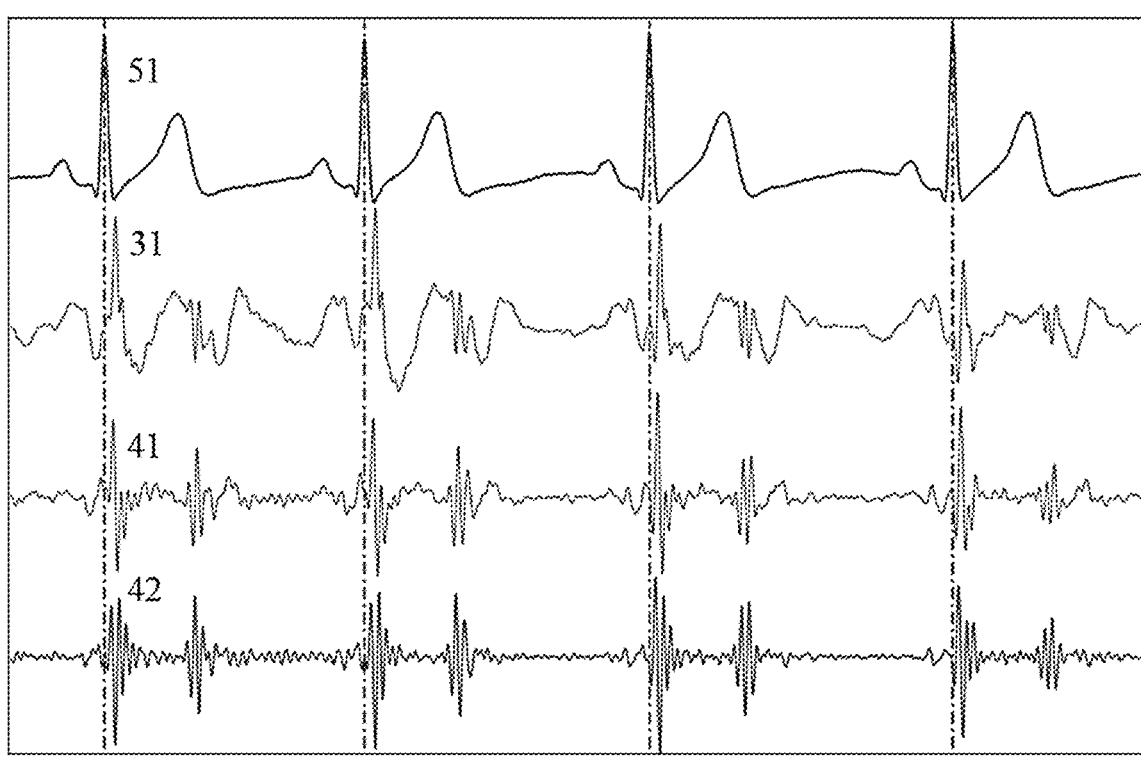
FIG. 5 is a waveform diagram for dividing cardiac cycles based on ECG information.

The heartbeat segmentation can be performed based on ECG: first, synchronously acquiring the vibration information of the subject and the electrophysiological activity information of the heart through an electrocardiogram sensor, which is called as electrocardiogram (ECG). Furthermore, since the ECG signals are relatively pure, has strong anti-interference and less noise, therefore, the hemodynamic related information, the first high-frequency component information or the second high-frequency component information can be segmented into heartbeats based on the ECG signals obtained synchronously with the vibration information. As shown in FIG. 5, the curve 51 is an electrocardiogram graph. Synchronizing the three curves in FIG. 4 with the electrocardiogram graph, and performing heartbeat segmentation of the vibration information with the assistance of ECG signals.

When the vibration information does not have the characteristics of order, regularity, and periodicity after being processed by one or more of the above-mentioned filtering processes, then needs to be further processed by one or more of the following methods, including but are not limited to: removing data segments of body motion, removing segments with poor signal quality, and so on. Specifically, segments with poor signal quality comprise: segments with poor waveform repeatability, unable to accurately identify heartbeats, with flat waveforms, or with few feature information, etc.

Figure 6:
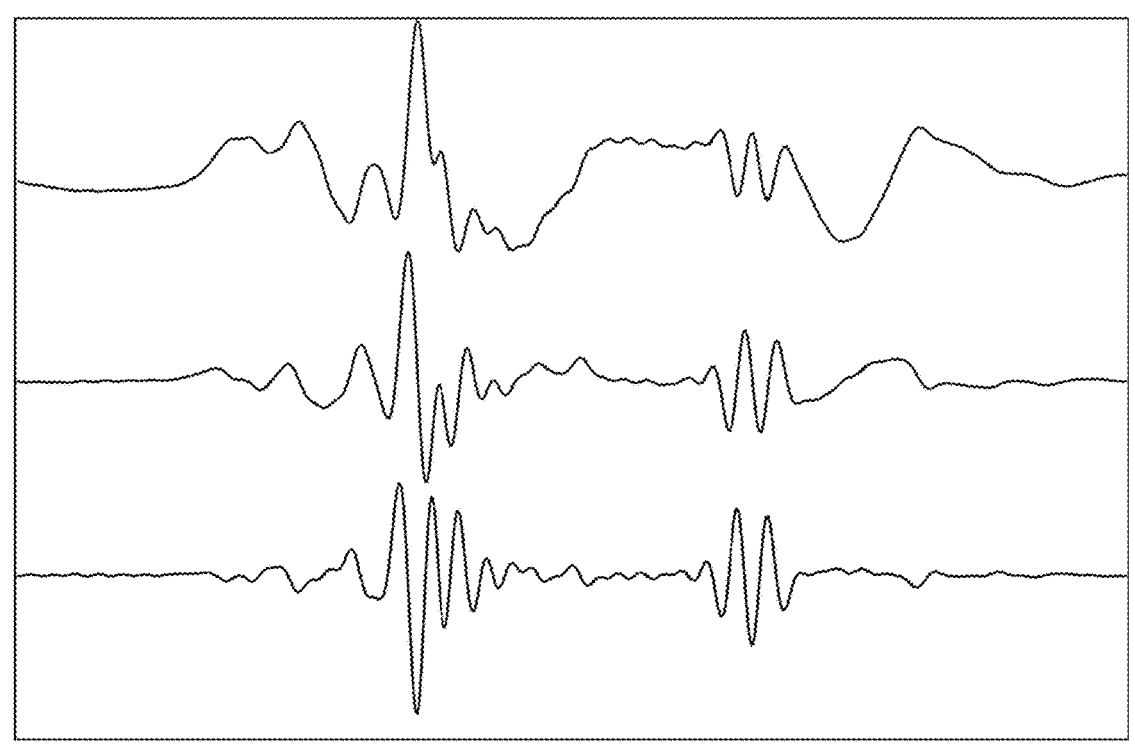
FIG. 6 is a diagram of a first wave group and a second wave group of the cardiac cycle.

In other examples, when the vibration information is obtained discretely in units of a cardiac cycle, heartbeat segmentation is not required, and S1032 can be omitted. As shown in FIG. 6, it is a waveform diagram of a cardiac cycle.

In the first embodiment of the present invention, a subsequent processing can comprise: processing the hemodynamic related information, the first high-frequency component information, and the second high-frequency component information in each heartbeat. The subsequent processing can also comprise: performing data superposition and average on the hemodynamic related information, the first high-frequency component information, or the second high-frequency component information within a preset period (for example, 30 minutes) according to the heartbeats to obtain the corresponding average information, and then performing a subsequent processing on the average information. Therefore, the hemodynamic related information, the first high-frequency component information, and the second high-frequency component information described below can refer to the data of a heartbeat, or the superposition and average data within a preset period according to the heartbeats.

S1033, determining a target wave group on the hemodynamic related information, the first high-frequency component curve, or the second high-frequency component curve.

In one embodiment of the present invention, S1033 can be implemented by the following two methods.
First Method First, generating vibration energy information based on the hemodynamic related information. Specifically, calculating the energy integral of the hemodynamic related information in a specified time window point by point to generate vibration energy information. A width of the time window can be 10 ms, 50 ms, 100 ms or other suitable widths; and the energy integral can be an absolute value, a square, a square root or other calculation methods after taking the average value. The vibration energy curve has two energy envelopes, which represent the energy accumulation during the systolic process and the early diastole of the heart.

Second, synchronizing the hemodynamic related information, the first high-frequency component information, or the second high-frequency component information and the vibration energy information on the same time axis; and determining the highest peak of the hemodynamic related information, the first high-frequency component information, or the second high-frequency component information, where the highest peak represents the shock caused by blood flowing into the aortic arch after aortic ejection; determining one energy envelope containing the highest peak as the first energy envelope, and the other energy envelope as the second energy envelope; determining a time window corresponding to the first energy envelope as the first-time window, and a time window corresponding to the second energy envelope as the second time window.

Finally, determining the waveforms of the hemodynamic related information, the first high-frequency component information, or the second high-frequency component information in the first-time window as the respective first wave group, the waveforms in the second time window as the respective second wave group, and the second wave group is the target wave group.
Second Method First, determining a starting time point of the isovolumic relaxation in the cardiac cycle, which specifically can be: simultaneously acquiring the subject's heart sound information and the vibration information on the body surface corresponding to the subject's thoracic cavity; and determining the starting time point of the second heart sound in the heart sound information as the starting time point of the isovolumic relaxation; or the second method can also be: obtaining an approximate heart sound information by polynomial fitting and smoothing filtering for the hemodynamic related information, and determining the starting time point of the second heart sound in the approximate heart sound information as the starting time of the isovolumic relaxation.

Second, determining wave cluster of the hemodynamic related information, the first high-frequency component information, or the second high-frequency component information within a preset time period after the start time point of the isovolumic relaxation as the target wave group. Where the preset time period can be any value between 50 ms and 120 ms, and the time period can be determined according to different groups of people.

Figure 7:
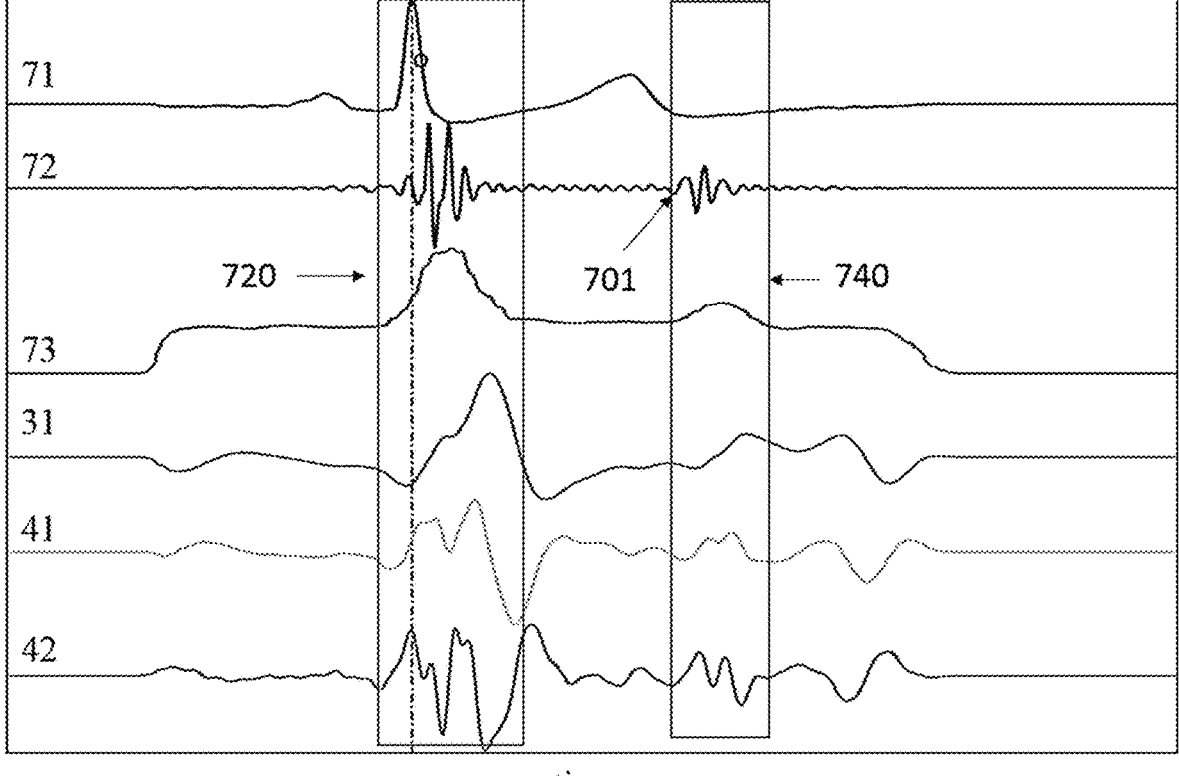
FIG. 7 is a diagram of the first wave group and the second wave group of the cardiac cycle divided by a combination of ECG information, heart sound information, and vibration energy information.

As shown in FIG. 7, synchronizing the synchronously acquired ECG information, heart sound information, and vibration energy information, as well as the three curves including the hemodynamic related information, the first high-frequency component curve, and the second high-frequency component curve on the same time axis. Where curve 71 is a time-domain waveform curve of ECG information, curve 72 is a time-domain waveform curve of heart sound information, and curve 73 is a time-domain waveform curve of vibration energy information. Curve 31, curve 41, and curve 42 corresponds to the waveforms of one cardiac cycle as shown in FIG. 4. In FIG. 7, the first wave group of each curve is represented as 720; and the second wave group, that is, the target wave group, is represented as 740. It should be understood that each of curve 31, curve 41 and curve 42 can determine the target wave group. The point 701 is the starting point of the second heart sound in the time-domain waveform curve of the heart sound information.

S104, determining the highest peak on the target wave group; determining a rising edge amplitude before the highest peak as a first characteristic value; and determining an amplitude between the highest peak and the subsequent lowest valley as a second characteristic value.

First, determining the highest peak on the target wave group, and then determining a first characteristic value as an amplitude of the rising edge before the highest peak, and determining a second characteristic value as an amplitude between the highest peak and the lowest valley thereafter in the target wave group.

Figure 8:
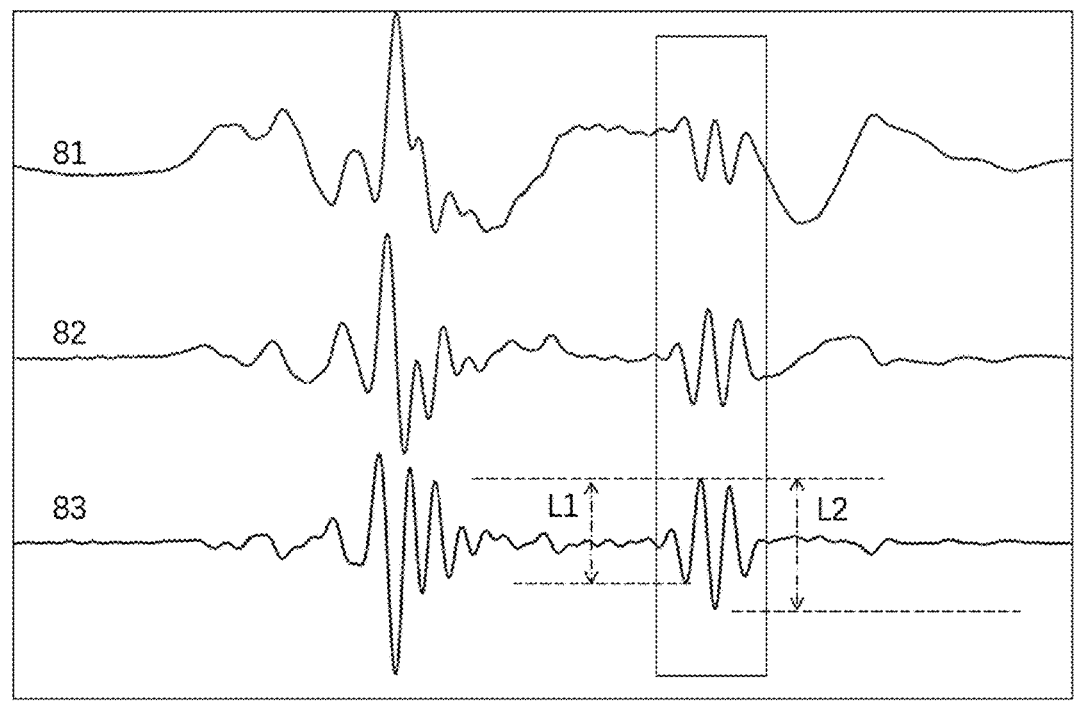
FIG. 8 is a diagram of a first characteristic value and a second characteristic value according to the vibration information of the subject B.
Figure 9:
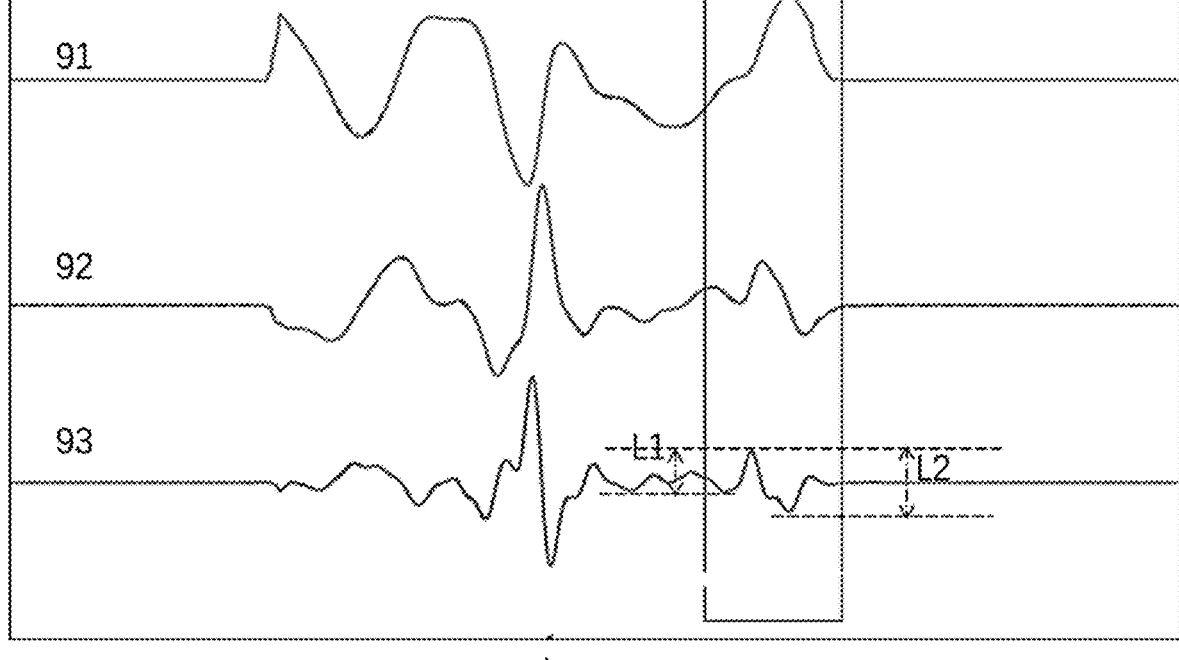
FIG. 9 is a diagram of the first characteristic value and the second characteristic value according to the vibration information of the subject C.
Figure 10:
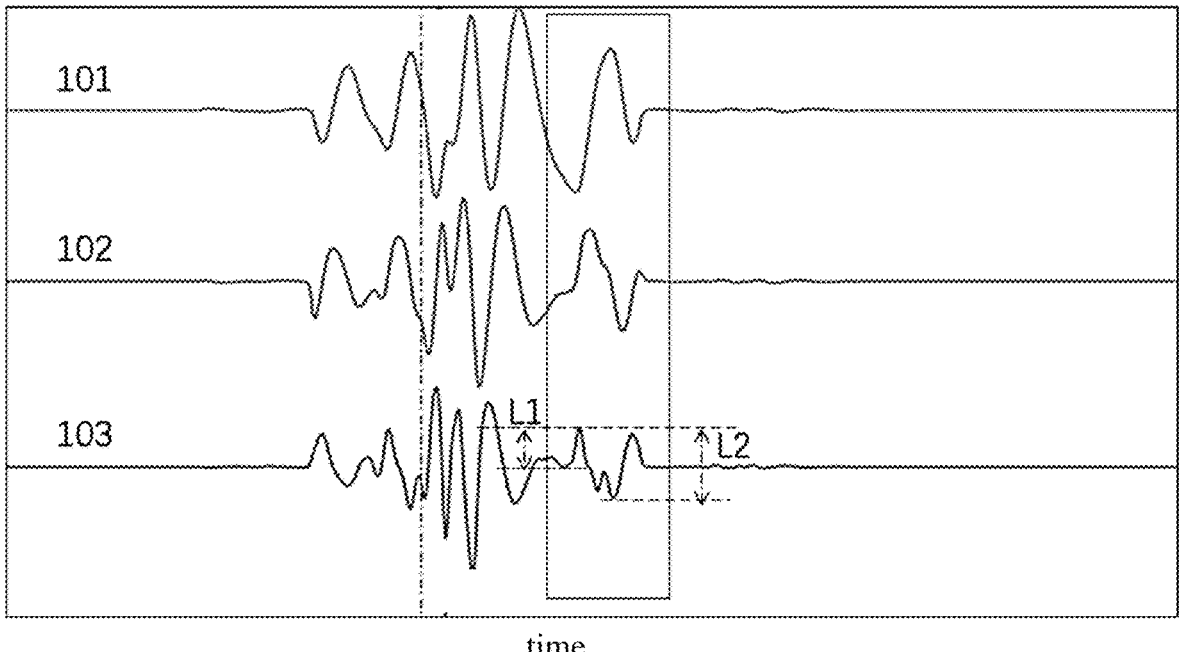
FIG. 10 is a diagram of the first characteristic value and the second characteristic value according to the vibration information of the subject D.
Figure 11:
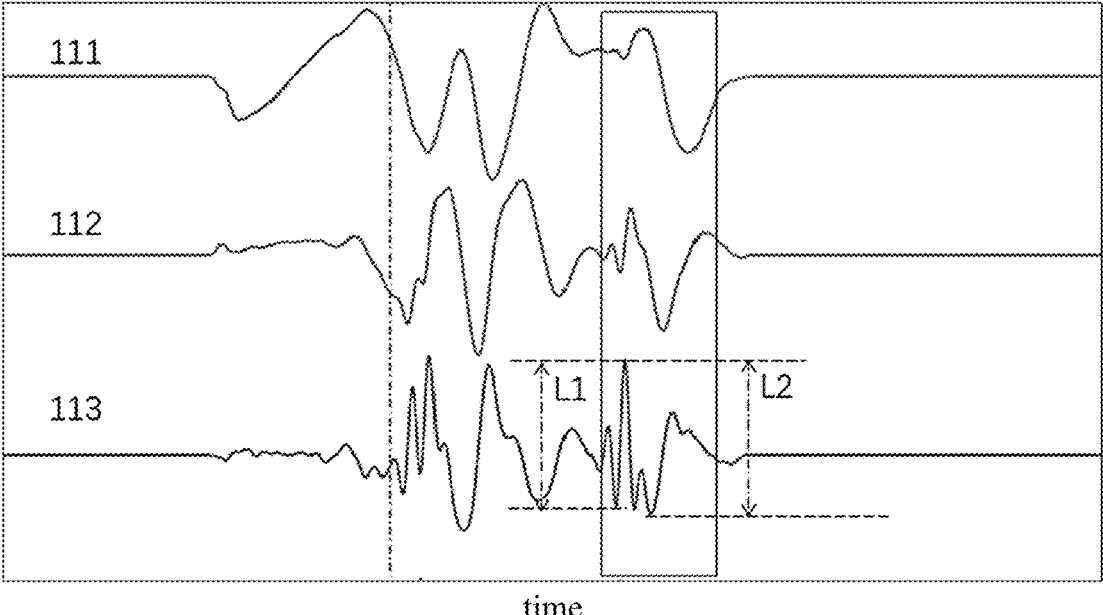
FIG. 11 is a diagram of the first characteristic value and the second characteristic value according to the vibration information of the subject E.

FIG. 8 illustrates the first characteristic value and the second characteristic value according to the vibration information of the subject B. FIG. 9 illustrates the first characteristic value and the second characteristic value according to the vibration information of the subject C. FIG. 10 illustrates the first characteristic value and the second characteristic value according to the vibration information of the subject D. FIG. 11 illustrates the first characteristic value and the second characteristic value according to the vibration information of the subject E. The curve 81 is the time-domain waveform curve of the hemodynamic related information of the subject B, the curve 82 is the time-domain waveform curve of the first high-frequency component information, and the curve 83 is the time-domain waveform curve of the second high-frequency component information. Where the horizontal axis represents time, and the vertical axis is dimensionless. In the same way, each curve in FIG. 9, FIG. 10, and FIG. 11 represents the same above. In each figure, L1 represents the first characteristic value, and L2 represents the second characteristic value.

S105, generating an indicating parameter based on the first characteristic value and the second characteristic value, and assessing a diastolic function of the subject based on the indicating parameter.

For example, a ratio of the second characteristic value to the first characteristic value may be used as the indicating parameter. When the indicating parameter is greater than a threshold, it is determined that the subject in an elevated filling pressure state. The elevated filling pressure state can be identified when ultrasound parameters: E/e'>14, Vtr>2.8 m/s, and E/A>1; and at this time, the heart is in a state of restrictive filling, ventricular relaxation is impaired and ventricular compliance is reduced. An elevated filling pressure will cause the heart into a rapid vicious circle, and timely intervention is required to avoid further deterioration.

Figure 12:
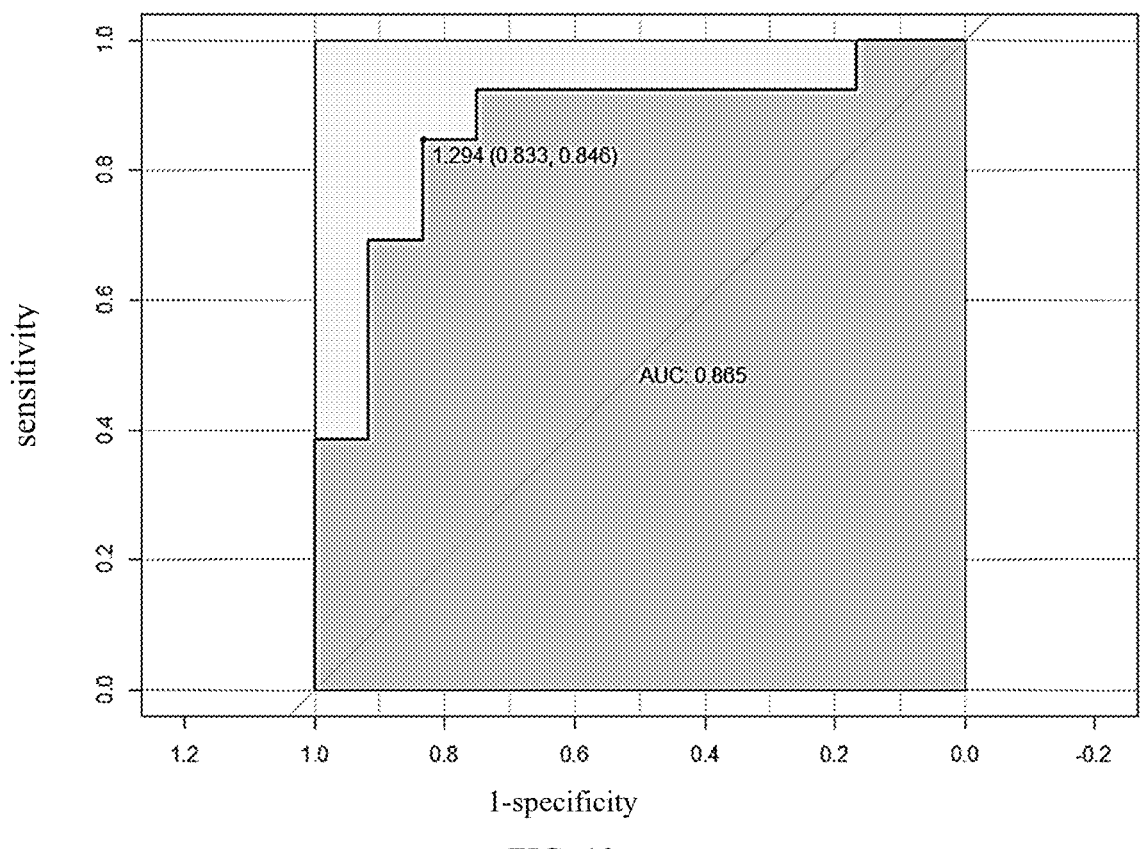
FIG. 12 is a ROC curve of the indicating parameter calculated based on the first high-frequency component.

Twenty-five heart failure patients as testing subjects were enrolled in a clinical study, where twelve patients with elevated filling pressure (marked as positive) and thirteen patients with non-high filling pressure (marked as negative). According to the above-mentioned diastolic function assessment method 100, calculating indicating parameters of the twenty-five subjects in the group based on their respective first high-frequency component curves. Analyzing sensitivity and specificity of the indicating parameters for the twenty-five subjects, and constructing the ROC curve as shown in FIG. 12. In FIG. 12, the area under the ROC curve is 0.865; the optimal Cut-off value is 1.294, and then the sensitivity and specificity are 84.6% and 83.3%, respectively.

Figure 13:
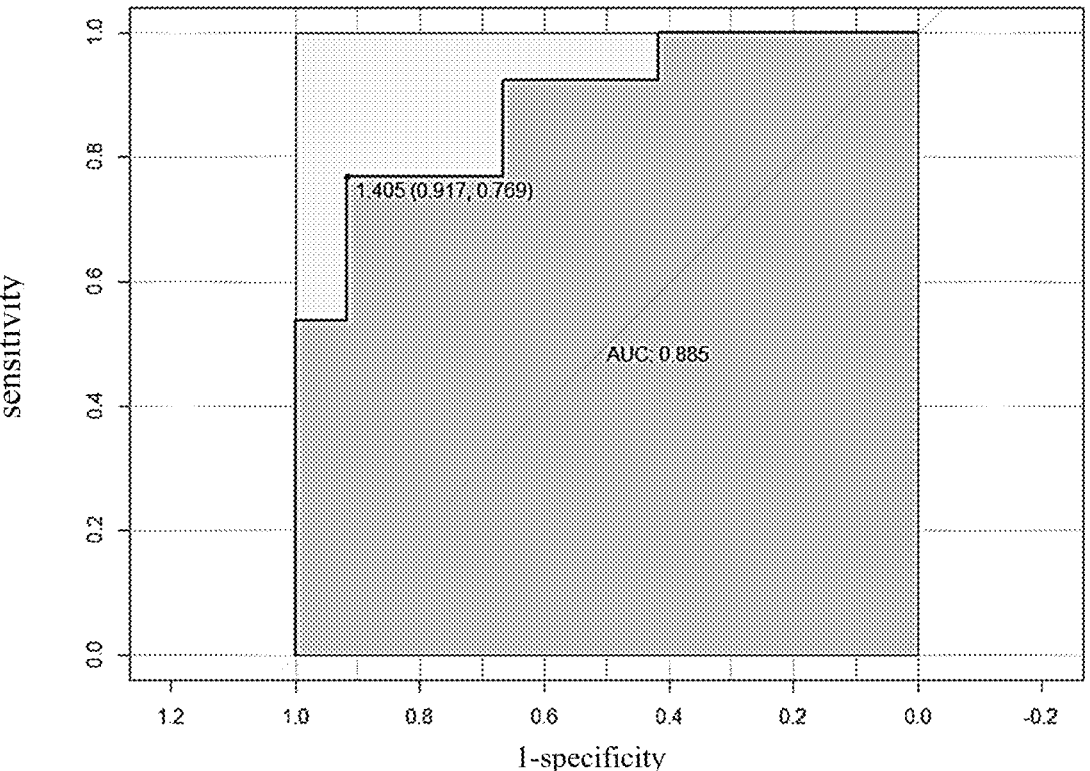
FIG. 13 is a ROC curve of the indicating parameter calculated based on the second high-frequency component.

Similarly, according to the above-mentioned diastolic function assessment method 100, calculating indicating parameters of the twenty-five subjects in the group based on their respective second high-frequency component curves to generate the ROC curve as shown in FIG. 13. In the ROC curve, the area under the ROC curve is 0.885; the optimal Cut-off value is 1.405; and the sensitivity and specificity are 76.9% and 91.7%, respectively. The threshold is determined based on people group with heart failure. In some embodiments of the present invention, the threshold may also be an absolute threshold, which is used to distinguish between healthy people and people with cardiac diastolic dysfunction. The threshold may also depend on the subject itself, for example, a relative threshold when diastolic function deteriorates can be obtained on the basis of the analysis of personal history data of the monitored subject.

Accordingly, for those of ordinary skill in the art, a diastolic function assessment method can be implemented using a ratio of the first characteristic value to the second characteristic value as an indicating parameter, which is also included in the protection scope of the present invention. In addition, those of ordinary skill in the art can easily obtain that, generating indicating parameters by performing other calculations on the first characteristic value and the second characteristic value, including but not limited to: addition, subtraction, multiplication, division, exponent, etc., which also belong to the scope of protection of the present invention.

In the first embodiment of the present invention, the diastolic function is represented by ventricular filling pressure, for example, an elevated filling pressure represents serious diastolic dysfunction. In addition, the diastolic function can also be represented by atrial pressure. The left ventricular filling pressure is related to the left atrial pressure and the pulmonary artery pressure due to the heart structure. Therefore, in some embodiments, the indicating parameters can be used to assess the filling pressure; the indicating parameters after a series of transformation calculation, can also be used to indirectly assess the left atrial pressure, the pulmonary artery pressure, and the degree of heart failure, etc., which are also within the protection scope of the present invention.

Second Embodiment

The second embodiment of the present invention provides a computer readable storage medium having computer programs stored thereon, which when being executed by a processor, cause the processor to perform the steps of the diastolic function assessment method of the present invention in the first embodiment.

Third Embodiment

Figure 14:
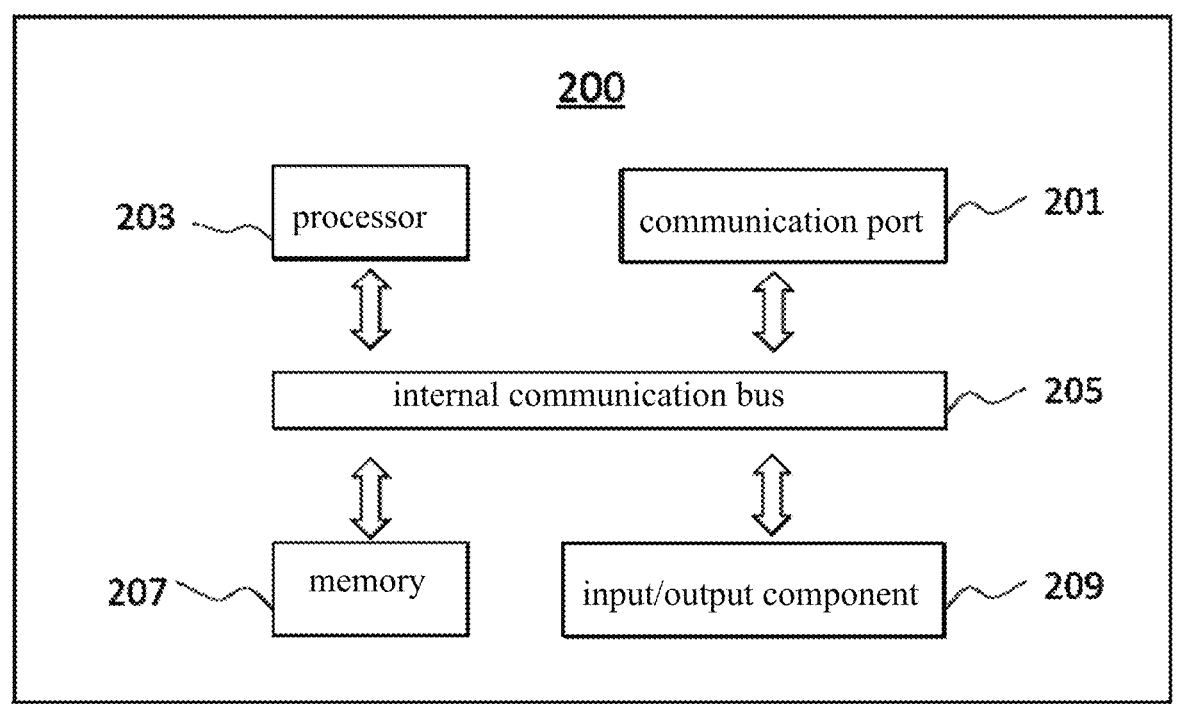
FIG. 14 is a block diagram of a diastolic function assessment device in accordance with a third embodiment of the present invention.

The third embodiment of the present invention provides a diastolic function assessment device. FIG. 14 illustrates a block diagram of a diastolic function assessment device 200. The diastolic function assessment device 200 may be a special computer device to process the vibration information acquired by the fiber-optic sensor.

For example, the diastolic function assessment device 200 may comprise a communication port 201 connected to a network for data communication. The diastolic function assessment device 200 may further comprise one or more processors 203 for executing computer instructions. The computer instructions may comprise, for example, routines, programs, objects, components, data structures, procedures, modules, and functions that perform the diastolic function assessment method described herein. For example, the processor 203 can obtain the vibration information of the fiber-optic sensor, and preprocess the vibration information to generate hemodynamic related information.

In some examples, the processors 203 may comprise one or more hardware processors, such as: a microcontroller, a microprocessor, a Reduced Instruction Set Computer (RISC), an Application Specific Integrated Circuit (ASIC), a Graphics Processing Unit (GPU)), Central Processing Unit (CPU), Digital Signal Processor (DSP), Field Programmable Gate Array (FPGA), Advanced RISC Machine (ARM), and Programmable Logic Device (PLD) etc., or any circuit or processor or a combination thereof capable of performing one or more functions.

The diastolic function assessment device 200 may comprise an internal communication bus 205, a memory 207 for processing and/or sending various data by the computer, and program instructions stored in other types of non-transitory storage media executed by the processor 203 in the memory 207. The method and/or process of the present invention can be implemented by program instructions. The diastolic function assessment device 200 also comprises an input/output component 209, which is used for input/output between the computer and other components (for example, User Interface Elements).

For ease of description, only one processor is described in the diastolic function assessment device 200 of the present invention. However, it should be noted that the diastolic function assessment device 200 of the present invention may also comprise multiple processors. Therefore, the process and/or method disclosed in the present invention may be executed by one processor as described in the present invention, and can also be executed jointly by multiple processors. For example, if the processor 203 of the diastolic function assessment device 200 in the present invention performs step A and step B, it should be understood that step A and step B can also be performed jointly or separately by two different processors (For example, a first processor executes step A, a second processor executes step B, or the first and second processors jointly execute steps A and B).

Fourth Embodiment

Figure 15:
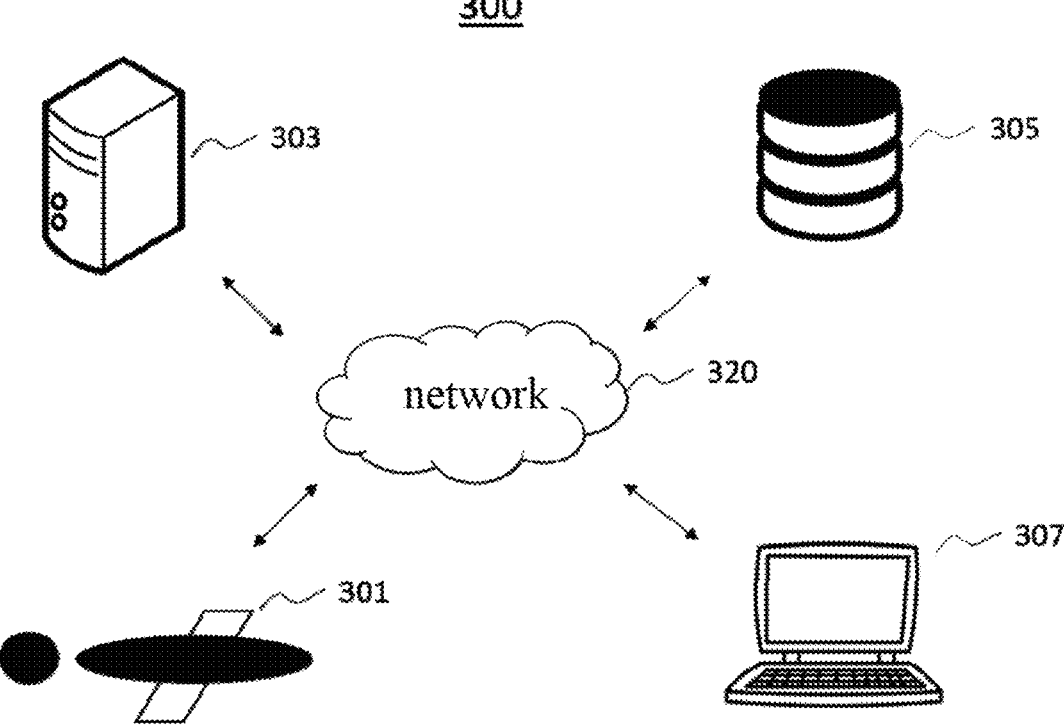
FIG. 15 is a block diagram of a diastolic function assessment system in accordance with a fourth embodiment of the present invention.

The fourth embodiment of the present invention provides a diastolic function assessment system, including:
  one or more vibration sensors; and the diastolic function assessment device provided in the third embodiment of the present invention.
  FIG. 15 illustrates a block diagram of a diastolic function assessment system 300, which may comprise one or more vibration sensors 301, one or more diastolic function assessment devices 303, and one or more storage devices 305.

Wherein, the vibration sensor 301 may be an acceleration sensor, a speed sensor, a displacement sensor, a pressure sensor, a strain sensor, or a stress sensor; and it may also be a sensor which converts physical quantities equivalently based on acceleration, speed, displacement, or pressure (such as an electrostatic charge sensor, an inflatable pressure sensor, a radar sensor, etc.). The strain sensor can be a fiber-optic sensor. When the vibration sensor 301 is a fiber-optic sensor, it can be placed under the subject's body. For example, the subject can be in a posture such as supine, prone, side-lying, etc. The fiber-optic sensor can be placed on the bed, and the subject is supine (prone or side-lying) on it. Those of ordinary skill in the art can understand that when the subject lies in the prone position, the subject's chest is the measurement position corresponding to the back of the subject in the supine position. In addition, the vibration sensor can also be placed on the contact surface behind the back of the subject in the supine posture at a certain tilt angle or on the contact surface behind the back of the subject leaning on a wheelchair or other leaning objects to acquire the vibration information.

The diastolic function assessment device 303 is as described in the third embodiment of the present invention, may be connected to the vibration sensor 301 through the network 320. The network 320 may be a single network, such as a wired network or a wireless network, or a combination of multiple networks. The network 320 may comprise, but is not limited to, a Local Area Network, a Wide Area Network, a shared internet, a dedicated internet, and the like. The network 320 may comprise a variety of network access points, such as wireless or wired access points, base stations, or network access points, through which other components of the diastolic function assessment system 300 can connect to the network 320 and transmit information through the network.

The storage device 305 may be configured to store data and instructions. The storage device 305 may comprise, but is not limited to, Random Access Memory, Read Only Memory, Programmable Read Only Memory, and the like. The storage device 305 may store information using electrical energy, magnetic energy, or optical methods, such as Hard Disks, Floppy Disks, Magnetic Core Memories, CDs, DVDs, and the like. The storage devices mentioned above are just a few examples, and the storage devices used by the storage device 305 are not limited to these.

In some examples, the diastolic function assessment system 300 may further comprise an output device 307 is used to output the result of the diastolic function assessment, and the output methods comprise but are not limited to graphics, text, data, voice, etc., such as one or more of graphic display, digital display, voice broadcast, braille display, etc. The output device 307 may be one or more of: a display, a mobile phone, a tablet computer, a projector, a wearable device (watch, earphone, glasses, etc.), a braille display, and the like. In some examples, the output device 307 can display the assessment result of the cardiac filling pressure of the subject 102 in real time. In other examples, the output device 307 can display a report in non-real time, which is the measurement result of the subject in a preset time period, for example, the user's cardiac filling pressure monitoring results during the sleeping time period. When monitoring a subject with heart failure, if a state of elevated filling pressure is assessed by the diastolic function assessment device, the subject with heart failure will face a worsening heart failure at this time and need to be hospitalized. The output device of the monitoring system can send reminders to the patient with heart failure, such as sending text messages, emails, phone calls, WeChat, and other instant messages; and can also send a message to the family doctor of the patient with heart failure, prompt that the patient may suffer from worsening heart failure to help doctors to make decisions. The system may further comprise a doctor-patient communication platform, and when the doctor receives the system notification that the patient may suffer from worsening heart failure, he can communicate with the patient in time.

For another example, the output device 307 can also implement an early warning, for example, a voice warning. When the diastolic function assessment device evaluates the diastolic function of the patient with heart failure being a state of elevated filling pressure, the patient with heart failure will suffer from worsening heart failure at this time, and the system can remind the patient to see a doctor in time by voice warning.

In the present invention, the method is used to monitor the diastolic function by acquiring the vibration information of the subject without intruding the body, is a passively measuring, and can realize continuous monitoring. The subject only needs to lie on the measuring device to perform the measurement, and no need for professional assistance. The method has the advantages of high measurement accuracy and simple operation, can improve the comfort of the tester, and can be applied to scenes such as hospitals and homes. The diastolic function assessment system provided in the present invention can evaluate the cardiac filling pressure of the subject, and then prompt a warning in advance when deterioration appear, so as to help the subject avoid deterioration.

A person of ordinary skill in the art can understand that all or part of the steps in the various methods of the above-mentioned embodiments can be completed by a program instructing relevant hardware. The program can be stored in a computer-readable storage medium. The computer-readable storage medium may comprise: ROM (Read Only Memory), RAM (Random Access Memory), magnetic disk or optical disk, etc.

The foregoing descriptions are only preferable embodiments of the present invention, and are not intended to limit the present invention. Any modification, equivalent replacement, and improvement made within the spirit and principle of the present invention shall be included in the protection scope of the present invention.

What is claimed is:

1. A diastolic function assessment method, performed by one or more processors executing one or more computer programs stored in a memory, comprising steps of:

non-invasively and continuously acquiring vibration information on a body surface corresponding to a thoracic cavity of a subject in a supine position through one or more fiber-optic sensors which are connected to the one or more processors; wherein the one or more fiber-optic sensors are configured to be placed under the subject's right shoulder and around the subject's right shoulder scapula, a sensing area of the one or more fiber-optic sensors is at least 20 square centimeters and covers the body surface area of the right shoulder scapula; optical fibers are distributed in the sensing area of the one or more fiber-optic sensors; the one or more fiber-optic sensors are sensitive to changes in vibration displacement; the vibration information contains breathing signals, hemodynamic signals, body motion signals and noise signals; a waveform of the vibration information includes breathing envelopes generated by the breathing signals; the hemodynamic signals, the body motion signals and the noise signals are superposed on the breathing envelopes; a horizontal axis of the waveform represents time, and a vertical axis represents normalized vibration information which is dimensionless;

preprocessing the vibration information to generate hemodynamic related information; comprising:

filtering the vibration information below 2 Hz to remove breathing signals and body motion signals and filtering the vibration information above 45 Hz to remove the noise signals, thereby generating the hemodynamic related information of 2-45 Hz;

performing a first-order differential processing on the hemodynamic related information to generate a first-order differential information with a frequency band of 2-45 Hz, performing a second-order differential processing on the hemodynamic related information to generate a second-order differential information with a frequency band of 2-45 Hz;

generating, by performing energy integration on the hemodynamic related information, vibration energy information comprising a first energy envelope and a second energy envelope which represent energy accumulation during a systolic process and an early diastole of the subject's heart;

synchronizing the hemodynamic related information, or the first-order differential information, or the second-order differential information, and the vibration energy information on the same time axis, and performing heartbeat segmentation;

determining, in one cardiac cycle, a highest peak of the hemodynamic related information, a highest peak of the first-order differential information, or a highest peak of the second-order differential information, wherein the highest peak of the hemodynamic related information or the first-order differential information or the second-order differential information represents a shock caused by blood flowing into an aortic arch after aortic ejection;

determining a target time window; wherein the first energy envelope contains the highest peak of the hemodynamic related information, or the highest peak of the first-order differential information, or the highest peak of the second-order differential information, while the second energy envelope does not have the highest peak of the hemodynamic related information, or the highest peak of the first-order differential information, or the highest peak of the second-order differential information; determine a time duration of the second energy envelope as the target time window;

determining, wave clusters within the target time window of the second-order differential information, as a target wave group;

determining a highest peak on the target wave group of the second-order differential information; determining a rising edge amplitude before the highest peak on the target wave group as a first characteristic value, and determining an amplitude between the same highest peak on the target wave group and a subsequent lowest valley on the target wave group as a second characteristic value;

generating an indicating parameter for assessing a diastolic function of the subject, comprising:

determining a ratio of the second characteristic value to the first characteristic value as the indicating parameter; and determining an elevated filling pressure state if the indicating parameter is greater than a threshold;

wherein the threshold is 1.405 or depends on a specific people group; and outputting, through an output device, a result of the assessing.

2. The method of claim 1, wherein the hemodynamic related information is:

data in one cardiac cycle; or data that is superimposed and averaged in a unit of cardiac cycle within a preset time period.

3. The method of claim 1, wherein the step of performing heartbeat segmentation comprises:

performing the highest peak or a lowest valley search on the hemodynamic related information, or the first-order differential information, or the second-order differential information at a search interval between 0.6 seconds and 1 second; and performing the heartbeat segmentation based on the repetitive highest peaks or the repetitive lowest valleys on the hemodynamic related information or the first-order differential information or the second-order differential information.

4. The method of claim 1, wherein the step of performing heartbeat segmentation comprises:

acquiring electrocardiography (ECG) data through an electrocardiogram sensor when acquiring the vibration information; and performing heartbeat segmentation on the hemodynamic related information or the first-order differential information or the second-order differential information based on the ECG data.

5. The method of claim 1, wherein the step of filtering the vibration information uses one or more of low-pass filtering, band-pass filtering, Infinite Impulse Response (IIR) filtering, Finite Impulse Response (FIR) filtering, wavelet filtering, zero-phase bidirectional filtering, polynomial smoothing filtering, integral transformation, and differential transformation, to filter the vibration information at least once to generate the hemodynamic related information.

6. A diastolic function assessment method, performed by one or more processors executing one or more computer programs stored in a memory, comprising steps of:

non-invasively and continuously acquiring the vibration information on the body surface corresponding to a thoracic cavity of a subject in a supine position through the one or more fiber-optic sensors configured to be placed under the subject's right shoulder and around a right shoulder scapula, a sensing area of the one or more fiber-optic sensors is at least 20 square centimeters and covers the body surface area of the right shoulder scapula of the subject; optical fibers are distributed in the sensing area of the one or more fiber-optic sensors;

preprocessing the vibration information to generate hemodynamic related information with a frequency band of 2-45 Hz; comprising: filtering, noise removal and signal scaling;

performing a first-order differential processing on the hemodynamic related information to generate a first-order differential information with a frequency band of 2-45 Hz, or, performing a second-order differential processing on the hemodynamic related information to generate a second-order differential information with a frequency band of 2-45 Hz;

generating, by performing energy integration on the hemodynamic related information, vibration energy information comprising a first energy envelope and a second energy envelope which represent energy accumulation during a systolic process and an early diastole of the subject's heart;

synchronizing the hemodynamic related information, or the first-order differential information, or the second-order differential information, and the vibration energy information on the same time axis, and performing heartbeat segmentation;

determining, in one cardiac cycle, a highest peak of the hemodynamic related information, or a highest peak of the first-order differential information, or a highest peak of the second-order differential information, wherein the highest peak of the hemodynamic related information or the first-order differential information or the second-order differential information represents a shock caused by blood flowing into an aortic arch after aortic ejection;

determining a target time window; wherein the first energy envelope contains the highest peak of the hemodynamic related information, or the highest peak of the first-order differential information, or the highest peak of the second-order differential information, while the second energy envelope does not have the highest peak of the hemodynamic related information, or the highest peak of the first-order differential information, or the highest peak of the second-order differential information; determine a time duration of the second energy envelope as the target time window; and determining wave clusters within the target time window of the first-order differential information as a target wave group;

determining a highest peak on the target wave group of the first-order differential information; determining a rising edge amplitude before the highest peak on the target wave group as a first characteristic value, and determining an amplitude between the same highest peak on the target wave group and a subsequent lowest valley on the target wave group as a second characteristic value;

generating an indicating parameter for assessing a diastolic function of the subject, comprising:

determining a ratio of the second characteristic value to the first characteristic value as the indicating parameter; and determining an elevated filling pressure state if the indicating parameter is greater than a threshold;

wherein the threshold is 1.294 or depends on a specific people group; and outputting, through an output device, a result of the assessing.

7. The diastolic function assessment method of claim 6, wherein the step of performing heartbeat segmentation comprises:

performing the highest peak or a lowest valley search on the hemodynamic related information, or the first-order differential information, or the second-order differential information at a search interval between 0.6 seconds and 1 second; and performing the heartbeat segmentation based on the repetitive highest peaks or the repetitive lowest valleys on the hemodynamic related information or the first-order differential information or the second-order differential information.

8. The diastolic function assessment method of claim 6, wherein the step of performing heartbeat segmentation comprises:

acquiring electrocardiography (ECG) data through an electrocardiogram sensor when acquiring the vibration information; and performing heartbeat segmentation on the hemodynamic related information or the first-order differential information or the second-order differential information based on the ECG data.

9. The diastolic function assessment method of claim 6, wherein the step of filtering uses one or more of low-pass filtering, band-pass filtering, Infinite Impulse Response (IIR) filtering, Finite Impulse Response (FIR) filtering, wavelet filtering, zero-phase bidirectional filtering, polynomial smoothing filtering, integral transformation, and differential transformation, to filter the vibration information at least once to generate the hemodynamic related information.

10. A diastolic function assessment system based on machine learning, comprising:

one or more processors, which are programmed to perform the steps of:

receiving vibration information on a body surface corresponding to a thoracic cavity of a subject in a supine position through one or more fiber-optic sensors which are connected to the one or more processors as input information for training;

analyzing the input information for training to establish an assessment model by machine learning, and;

receiving the vibration information on the body surface corresponding to the subject's thoracic cavity through the one or more fiber-optic sensors; and performing an assessment to the subject's diastolic function by the assessment model;

wherein the one or more fiber-optic sensors are configured to be placed under the subject's right shoulder and around the subject's right shoulder scapula, a sensing area of the one or more fiber-optic sensors is at least 20 square centimeters and covers the body surface area of the right shoulder scapula; optical fibers are distributed in the sensing area of the one or more fiber-optic sensors; the one or more fiber-optic sensors are sensitive to changes in vibration displacement; the vibration information contains breathing signals, hemodynamic signals, body motion signals and noise signals; a waveform of the vibration information includes breathing envelopes generated by the breathing signals; the hemodynamic signals, the body motion signals and the noise signals are superposed on the breathing envelopes; a horizontal axis of the waveform represents time, and a vertical axis represents normalized vibration information which is dimensionless;

wherein the assessment model performs steps of:

preprocessing the vibration information to generate hemodynamic related information; comprising:

filtering the vibration information below 2 Hz to remove breathing signals and body motion signals and filtering the vibration information above 45 Hz to remove the noise signals, thereby generating the hemodynamic related information of 2-45 Hz;

performing a first-order differential processing on the hemodynamic related information to generate a first-order differential information, or, performing a second-order differential processing on the hemodynamic related information to generate a second-order differential information;

generating, by performing energy integration on the hemodynamic related information, vibration energy information comprising a first energy envelope and a second energy envelope which represent energy accumulation during a systolic process and an early diastole of the subject's heart;

synchronizing the hemodynamic related information, or the first-order differential information, or the second-order differential information, and the vibration energy information on the same time axis, and performing heartbeat segmentation;

determining, in one cardiac cycle, a highest peak of the hemodynamic related information, or a highest peak of the first-order differential information, or a highest peak of the second-order differential information, wherein the highest peak of the hemodynamic related information or the first-order differential information or the second-order differential information represents a shock caused by blood flowing into an aortic arch after aortic ejection;

determining a target time window; wherein the first energy envelope contains the highest peak of the hemodynamic related information, or the highest peak of the first-order differential information, or the highest peak of the second-order differential information, while the second energy envelope does not have the highest peak of the hemodynamic related information, or the highest peak of the first-order differential information, or the highest peak of the second-order differential information; determine a time duration of the second energy envelope as the target time window; and determining, wave clusters within the target time window of the first-order differential information or the second-order differential information, as a target wave group;

determining a highest peak on the target wave group of the first-order differential information or the second-order differential information; determining a rising edge amplitude before the highest peak on the same target wave group as a first characteristic value and determining an amplitude between the same highest peak on the same target wave group and a subsequent lowest valley on the same target wave group as a second characteristic value; and generating an indicating parameter for assessing a diastolic function of the subject, comprising:

determining a ratio of the second characteristic value to the first characteristic value as the indicating parameter; and determining an elevated filling pressure state if the indicating parameter is greater than a threshold;

wherein the threshold is 1.294 when determining the first characteristic value and the second characteristic value based on the first-order differential information; and the threshold is 1.405 when determining the first characteristic value and the second characteristic value based on the second-order differential information; or the threshold depends on a specific people group.

11. The diastolic function assessment system based on machine learning of claim 10, wherein the step of performing heartbeat segmentation comprises:

performing the highest peak or a lowest valley search on the hemodynamic related information, or the first-order differential information, or the second-order differential information at a search interval between 0.6 seconds and 1 second; and performing the heartbeat segmentation based on the repetitive highest peaks or the repetitive lowest valleys on the hemodynamic related information or the first-order differential information or the second-order differential information.

12. The diastolic function assessment system based on machine learning of claim 10, wherein the step of performing heartbeat segmentation comprises:

acquiring electrocardiography (ECG) data through an electrocardiogram sensor when acquiring the vibration information; and performing heartbeat segmentation on the hemodynamic related information or the first-order differential information or the second-order differential information based on the ECG data.

13. The diastolic function assessment system based on machine learning of claim 10, wherein the step of filtering the vibration information uses one or more of low-pass filtering, band-pass filtering, Infinite Impulse Response (IIR) filtering, Finite Impulse Response (FIR) filtering, wavelet filtering, zero-phase bidirectional filtering, polynomial smoothing filtering, integral transformation, and differential transformation, to filter the vibration information at least once to generate the hemodynamic related information.

\* \* \* \* \*